United States Patent [19]
Nichels et al.

[11] Patent Number: 5,112,865
[45] Date of Patent: May 12, 1992

[54] PHARMACEUTICAL COMPOSITIONS CONTAINING A DERIVATIVE OF 3-HYDROXYBUTANOIC ACID CHOSEN FROM OLIGOMERS OF THIS ACID AND ESTERS OF THIS ACID OR OF THESE OLIGOMERS WITH 1,3-BUTANEDIOL

[75] Inventors: William Nichels, Vilvoorde; Philippe d'Oultremont, Blicquy, both of Belgium

[73] Assignee: Solvay & Cie (Société Anonyme), Brussels, Belgium

[21] Appl. No.: 568,546

[22] Filed: Aug. 15, 1990

Related U.S. Application Data

[63] Continuation of Ser. No. 269,891, Nov. 9, 1988, abandoned.

[30] Foreign Application Priority Data

Nov. 19, 1987 [BE] Belgium ............................... 8701314

[51] Int. Cl.⁵ ...................... A61K 31/22; A61K 31/19
[52] U.S. Cl. ...................................... 514/546; 514/547
[58] Field of Search ................................ 514/546, 547

[56] References Cited

U.S. PATENT DOCUMENTS 4,365,088 12/1982 Vanlautem et al. ................. 562/579
4,574,085 3/1986 Dolkart et al. ......................... 514/23

FOREIGN PATENT DOCUMENTS 0249667 12/1987 European Pat. Off. .
WO/8203987 11/1982 PCT Int'l Appl. .

OTHER PUBLICATIONS

J. Marsh, Advanced Organic Chemistry, pp. 334–338 (1985) Third Edition.
Holmes, Chem. Abs. 104, 230469c (1984).
Kamata, Chem. Abs., 104, 39779b (1985).
Lafferty, Chem. Abs. 104, 223562 (1984; abstract published in 1986).

*Primary Examiner*—Mark L. Berch
*Attorney, Agent, or Firm*—Spencer, Frank & Schneider

[57] ABSTRACT

The invention relates to a solution for dialysis containing a derivative of 3-hydroxybutanoic acid chosen from oligomers of this acid and esters of this acid or of these oligomers with 1,3-butanediol.

12 Claims, No Drawings

PHARMACEUTICAL COMPOSITIONS CONTAINING A DERIVATIVE OF 3-HYDROXYBUTANOIC ACID CHOSEN FROM OLIGOMERS OF THIS ACID AND ESTERS OF THIS ACID OR OF THESE OLIGOMERS WITH 1,3-BUTANEDIOL

This application is a continuation of application Ser. No. 07/269,891, filed Nov. 9th, 1988 now abandoned.

BACKGROUND OF THE INVENTION

1. Field of the Invention

The present invention relates to pharmaceutical compositions which are suitable, in particular, for blood purification, especially of dialysis solutions employed during treatments applied in individuals suffering from renal insufficiency.

2. Technology Review

A number of kidney diseases lead to chronic renal insufficiency, the capacity for concentrating the urine and the possibilities of excretion being impaired; this results in cardiovascular, digestive and neuromuscular disorders. When a transplantation cannot be performed, haemodialysis and peritoneal dialysis make it possible to compensate for renal function. Acute renal insufficiency, certain types of poisoning, hepatic coma and severe electrolytic disorders may also be treated by dialysis.

Solutions for dialysis generally contain an osmotic agent, ions and a substance having buffering power, as well as various optional additives.

The most commonly used osmotic agent is glucose; however, a portion of this glucose can cross the peritoneal membrane, so that the patient absorbs 50 to 300 g of it per day. This phenomenon causes serious problems during the dialysis of some patients; thus, it can interfere with the treatment of diabetic patients and promote the appearance of lipid disorders and obesity.

To remedy these drawbacks, it has been proposed to add insulin to the dialysis solution or to employ other osmotic agents such as other sugars or polyols. However, these products also have drawbacks: they are toxic, accumulate, or cause a polyurea or a rise in lactic acid. Thus, for example, glycerol, which has been proposed in International Application No. Pct/U.S. 82/00488, passes rapidly across the peritoneal membrane and makes it necessary to resort to higher concentrations than those of glucose, which eventually lead to a weight gain by the patient.

A pharmaceutical composition that is usable for blood purification, and which enables these drawbacks to be remedied, has now been found.

SUMMARY OF THE INVENTION

To this end, the present invention relates to a pharmaceutical composition, a solution containing a derivative of 3-hydroxybutanoic acid chosen from oligomers of this acid and esters of this acid or of these oligomers with 1,3-butanediol.

The oligomers of 3-hydroxybutanoic acid present in the compositions according to the invention may be of any type. In general, they are water-soluble at room temperature and at atmospheric pressure. Preferably, oligomers consisting exclusively or having a high content of dimers and/or trimers are employed.

Esters of 3-hydroxybutanoic acid or of these oligomers with 1,3-butanediol are understood to mean any ester formed from these compounds, irrespective of the type of isomer employed. Thus, the ester may be formed from either of the alcohol groups of the butanediol, that is to say 3-hydroxy-1-butyl 3-hydroxybutanoate and 4-hydroxy-2-butyl 3-hydroxybutanoate, also known as 1,3-butanediol 3-mono(3'-hydroxybutyrate) and 1,3-butanediol 1-mono(3'-hydroxybutyrate).

The 3-hydroxybutanoic acid from which the oligomers and the esters present in the compositions according to the invention are derived may be of various isomeric forms, such as the L(+), D(−) and racemic forms. Preferably, however, it is of the D(−) isomeric form.

D(−)-3-Hydroxybutanoic acid and the oligomers of this acid may advantageously be obtained by the depolymerization of natural polymers extracted from biomasses according to processes such as, in particular, those described in European Patent 0,043,620.

The esters of 3-hydroxybutanoic acid or of the oligomers of this acid with 1,3-butanediol may be prepared by any suitable organic synthesis.

These esters may, in particular, be prepared by the processes described in German Patent Applications German Offenlegungsschrift 2,500,310 and German Offenlegungsschrift 2,500,312.

The 1,3-butanediol included in these esters may be of various isomeric forms, such as the L(+), D(−) and/or racemic forms.

The compositions according to the invention may be used as medicinal products, and in particular for the treatment and prevention in human medicine and in veterinary medicine of conditions necessitating dialysis. In this case, they are formulated for use as a pharmaceutical means intended for internal or external treatment. The derivatives of 3-hydroxybutanoic acid according to the invention are used for obtaining a medicinal product intended for therapeutic use for the purpose of blood purification or for the manufacture of means intended for the preparation of solutions for blood purification.

The compositions can contain one or more derivatives of 3-hydroxybutanoic acid, and usually contain formulation additives that enable them to be administered in a convenient manner.

Usually, the compositions according to the invention take the form of a dialysis solution. This aqueous solution is at a physiological pH and can contain various substances having buffering power, such as weak acids with their conjugate weak bases, in particular lactate, acetate, acetoacetate, citrate and bicarbonate, and various physiological salts in the form of ions such as, in particular, $Cl^-$, $K^+$, $Na^+$, $Ca^{++}$ and $Mg^{++}$. These salts are present in the dialysis solutions at concentrations enabling any depletion or overload to be avoided; that is to say, at a sufficient concentration to be osmotically compatible with the blood.

The pharmaceutical compositions according to the invention can contain other active principles for blood purification, especially other osmotic agents employed in solutions for dialysis. Among these agents, sugars, polyols or other substances such as amino acids, gelatin and hydrolysed starch may be mentioned by way of examples.

The concentration of the derivatives of 3-hydroxybutanoic acid employed in the compositions according to the invention is chosen in such a way that the osmotic strength and the osmolarity (number of particles expressed in millimoles) are compatible with the body being treated. In general, the osmolarity of the dialysis solution is between 250 and 700 milliosmoles per liter, preferably between 275 and 600 and, as a matter of special preference, between 300 and 500 milliosmoles per liter.

Preferably, the concentration of the derivatives of 3-hydroxybutanoic acid employed in the compositions according to the invention is between 0.5 and 200 g per liter of dialysis solution and, as a matter of special preference, between 1 and 100 g/l.

The derivatives of 3-hydroxybutanoic acid can replace glucose in all dialysis solutions; they constitute readily metabolized non-toxic osmotic agents which do not cause metabolic disturbance and do not adversely affect the peritoneal membrane. They are especially favourable in the dialysis of patients suffering from sugar diabetes.

The dialysis solution according to the invention is suitable for haemodialysis, peritoneal dialysis, continuous ambulatory peritoneal dialysis and intermittent peritoneal dialysis.

The invention is illustrated by the examples which follow.

EXAMPLE 1

A solution is prepared for peritoneal dialysis by dissolving in 1 l of sterile and pyrogen-free pure water 5.67 g of sodium chloride, 3.92 g of sodium lactate, 0.257 g of calcium chloride dihydrate, 0.152 g of magnesium chloride hexahydrate and 1.32 g of 3-hydroxy-1-butyl D(−)-3-hydroxybutanoate.

This solution is sterilized by filtration and/or by heat.

The osmolarity of this solution is approximately 279 milliosmoles/l.

EXAMPLE 2

A solution for peritoneal dialysis is prepared by dissolving in 1 l of sterile and pyrogen-free pure water 5.55 g of sodium chloride, 1.96 g of sodium lactate, 0.257 g of calcium chloride dihydrate, 0.152 g of magnesium chloride hexahydrate, 1.42 g of sodium succinate and 6 g of D(−)-3-hydroxybutanoic acid dimer.

The osmolarity of this solution is approximately 330 milliosmoles/l.

EXAMPLE 3

A solution is prepared for peritoneal dialysis, intended for purifying the blood of patients suffering from renal insufficiency by the removal of nitrogenous wastes, potassium, phosphates, water and extracellular volume, and for correcting acidosis by the provision of buffering substances.

5.85 g of sodium chloride, 4.75 g of sodium acetate trihydrate 0.384 g of calcium chloride 6 H$_2$O, 0.153 g of magnesium chloride 6 H$_2$O and 14.5 g of 4-hydroxy-2-butyl D(−)-3-hydroxybutanoate are mixed in 1 liter of sterile and pyrogen-free pure water.

The osmolarity of this solution is approximately 360 milliosmoles/l.

This solution is sterilized.

EXAMPLE 4

A solution for intermittent peritoneal dialysis is prepared by dissolving in 1 liter of sterile and pyrogen-free pure water 5.85 g of sodium chloride, 4.75 g of sodium acetate trihydrate 0.384 g of calcium chloride hexahydrate 0.153 g of magnesium chloride hexahydrate and 67.5 g of D(−)-3-hydroxybutanoic acid trimer.

This solution is sterilized.

The osmolarity of this solution is approximately 500 milliosmoles/l.

We claim:

1. A dialysis solution consisting essentially of sterile water, formulation additives and an effective osmotic amount of a member selected from the group consisting of a derivative of 3-hydroxybutanoic acid chosen from dimers and/or trimers of 3-hydroxybutanoic acid, an ester of a dimer and/or trimer of 3-hydroxybutanoic acid with 1,3-butanediol, and an ester of 3-hydroxybutanoic acid with 1,3-butanediol.

2. The dialysis solution according to claim 1, wherein said derivative of 3-hydroxybutanoic acid is derived from the D(−) isomeric form of 3-hydroxybutanoic acid.

3. The dialysis solution according to claim 1, wherein said derivative of 3-hydroxybutanoic acid has a concentration of about 0.5 to 200 grams per liter.

4. The dialysis solution according to claim 3, wherein said derivative of 3-hydroxybutanoic acid has a concentration of about 1 to 100 grams per liter.

5. A glucose-free dialysis solution consisting of sterile water, formulation additives and an effective osmotic amount of a member selected from the group consisting of a derivative of 3-hydroxybutanoic acid chosen from dimers and/or trimers of 3-hydroxybutanoic acid, an ester of a dimer and/or trimer of 3-hydroxybutanoic acid with 1,3-butanediol, and an ester of 3-hydroxybutanoic acid with 1,3-butanediol.

6. The solution according to claim 5, wherein said derivative of 3-hydroxybutanoic acid is derived from the D(−) isomeric form of 3-hydroxybutanoic acid.

7. The dialysis solution according to claim 5, wherein said derivative of 3-hydroxybutanoic acid has a concentration of 0.05 to 200 grams per liter.

8. The dialysis solution according to claim 7, wherein said derivative of 3-hydroxybutanoic acid has a concentration of 1 to 100 grams per liter.

9. An aqueous dialysis solution of physiological pH consisting essentially of sterile water, formulation additives, physiological salts osmotically compatible with blood, and an effective osmotic amount of a member selected from the group consisting of a derivative of 3-hydroxybutanoic acid chosen from dimers and/or trimers of 3-hydroxybutanoic acid, an ester of a dimer and/or trimer of 3-hydroxybutanoic acid with 1,3-butanediol, and an ester of 3-hydroxybutanoic acid with 1,3-butanediol.

10. The aqueous dialysis solution according to claim 9, wherein said derivative of 3-hydroxbutanoic acid is derived from the D(−) isomeric form of 3-hydroxybutanoic acid.

11. The dialysis solution according to claim 9, wherein said derivative of 3-hydroxybutanoic acid has a concentration of 0.5 to 200 grams per liter.

12. The dialysis solution according to claim 11, wherein said derivative of 3-hydroxybutanoic acid has a concentration of 1 to 100 grams per liter.

* * * * *